(12) United States Patent
Lane (10) Patent No.: US 7,766,853 B2
(45) Date of Patent: Aug. 3, 2010

(54) PERIPHERAL ACCESS DEVICES AND SYSTEMS

(75) Inventor: Rodney James Lane, New South Wales (AU)

(73) Assignee: Droneon Pty Limited, St. Leonards (AU)

( * ) Notice: Subject to any disclaimer, the term of this patent is extended or adjusted under 35 U.S.C. 154(b) by 22 days.

(21) Appl. No.: 11/662,117

(22) PCT Filed: Aug. 25, 2005

(86) PCT No.: PCT/AU2005/001300

§ 371 (c)(1),
(2), (4) Date: Jul. 10, 2007

(87) PCT Pub. No.: WO2006/026805

PCT Pub. Date: Mar. 16, 2006

(65) Prior Publication Data

US 2008/0171961 A1    Jul. 17, 2008

(30) Foreign Application Priority Data

Sep. 7, 2004   (AU) .............................. 2004905108
Mar. 11, 2005  (AU) .............................. 2005901205
Aug. 2, 2005   (AU) .............................. 2005904147

(51) Int. Cl.
*A61M 37/00* (2006.01)

(52) U.S. Cl. .................... 604/4.01; 604/6.06; 604/6.11; 604/6.16; 604/196; 600/16; 600/17; 600/18; 606/194; 128/898

(58) Field of Classification Search ................. 604/4.01, 604/6.06, 6.1, 6.11, 6.16
See application file for complete search history.

(56) References Cited

U.S. PATENT DOCUMENTS

| 4,851,054 A | 7/1989 | Fukuzuka et al. ............. 148/624 |
| 4,857,054 A * | 8/1989 | Helfer ...................... 604/99.03 |
| 6,083,215 A | 7/2000 | Milavetz ..................... 604/509 |
| 6,315,768 B1 | 11/2001 | Wallace ...................... 604/507 |
| 2004/0019310 A1 | 1/2004 | Hogendijk ...................... 604/1 |

FOREIGN PATENT DOCUMENTS

| WO | WO 0038763 | 7/2000 |
| WO | WO 0041640 | 7/2000 |

OTHER PUBLICATIONS

"International Search Report," Australian Patent Office, Nov. 1, 2005, 3 pages.

* cited by examiner

*Primary Examiner*—Tatyana Zalukaeva
*Assistant Examiner*—Ilya Y Treyger
(74) *Attorney, Agent, or Firm*—Woodcock Washburn LLP (57) ABSTRACT

A cannulation system (10) for perfusing a patient's circulatory system, includes an inflow cannula (14) having a first end adapted to be connected to said circulatory system and a second end adapted to be connected to a blood pump (19), an outflow cannula (23) having a first end adapted to be connected to the blood pump (19) and a second end adapted to be connected to said circulatory system at a location downstream of the first end of the inflow cannula. The flow of blood from the pump (19) is in series with the normal blood flow of the circulatory system of the patient and creates a localized region of hypertension.

12 Claims, 11 Drawing Sheets

PERIPHERAL ACCESS DEVICES AND SYSTEMS

TECHNICAL FIELD

The present invention relates generally to peripheral access devices and systems which can provide intermittent or acute access to a patient's circulatory system for the purpose of hyper-perfusion.

BACKGROUND ART

The access devices and systems of the invention will find use in distal regions and in arteries other than distal including the right and left internal mammary arteries (RIMA, LIMA), coronary arteries, and bypass grafts. Thus, the devices and systems of the invention may be used to hypeperfuse any vessel (natural, man made or of animal origin) in the body.

There is a pressing need for a device that is capable of supplementing blood perfusion in a patient's circulatory system. It is common in patients suffering from Congestive Heart Failure ("CHF"), diabetes, gangrene, erectile dysfunction, atheroma or obstructive vessel disease to also suffer from poor circulation. Poor circulation often leads to a patient suffering from ischaemia or chronic oxygen debt in their circulatory system. This ischaemia or oxygen debt that can lead to exercise related claudication or rest pain. These diseases may also lead to various other complications that may require radical surgery to correct, such as amputation of limbs.

Traditionally, poor circulation in limbs has been treated by a wide range of devices and procedures, which were aimed at promoting blood flow through a limb and by doing so, induce revascularisation of the limb.

In the past, hyperbaric chambers have been used to increase oxygen tension within the limbs. This increases oxygen tension delivered to distal regions of the patient's circulatory system and leads to a reduction of oxygen debt in these regions. Hyperbaric chambers are often expensive, inefficient, reduce the patient's quality of life and are suitable only for short term use.

It is an object of the present invention to address or ameliorate one or more of the abovementioned disadvantages and to address the problem of supplementing blood perfusion in a patient's circulatory system.

DISCLOSURE OF INVENTION

According to one aspect of the invention, there is provided a system of cannulation for perfusing a patient's circulatory system, said system of cannulation comprising:
  (i) an inflow cannula having a first end adapted to be connected to the circulatory system and a second end adapted to be connected to a blood pump, and
  (ii) an outflow cannula having a first end adapted to be connected to the blood pump and a second end adapted to be connected to the circulatory system at a location downstream of the first end of the inflow cannula, the arrangement being such that blood flow from the pump is in series with the normal blood flow of the circulatory system of the patent and creates a localised region of hypertension.

In a preferred form of the invention, the outflow cannula is divided to provide two outlets.

The system may be connected to a distal region which may include a portion of the arterial blood supply of the circulatory system and the system may include at least one additional outlet for connection to a haemodialysis system.

The blood pump may be located in a position remote from the heart of the patient.

In a preferred form of the invention, the inflow and outflow cannula incorporate a high pressure circulatory access device which facilitates access to the circulatory or arterial system.

The high pressure circulatory access device may include a slidable plunger to occlude said respective inlet or outlet cannula, as desired. The slidable plunger may also be lockable in an open or a closed position.

The system may also include an occlusion device to be inserted between high and low pressure sides of the said system and said occlusion device may be selectively controlled, transcutaneously.

It is preferable for the system to supply a continuous suprasystolic pressure in both systole and diastole. The system may also allow for the attachment to any type of blood pump. Preferably, at least a portion of the system allows simultaneous infusion of pharmaceuticals.

According to another aspect of the invention there is provided a blood pumping system for perfusing of a patient's circulatory system, said blood pumping system comprising:—
  (i) a blood pump,
  (ii) an inflow cannula having a first end adapted to be connected to said circulatory system and a second end connected to the blood pump, and
  (iii) an outflow cannula having a first end connected to the blood pump and a second end adapted to be connected to said circulatory system at a location downstream from the first end of the inflow cannula, the arrangement being such that the blood flow from the pump is in series with the normal blood flow of the circulatory system of the patient and creates a localised hypertensive region.

The system may be connected to a distal region which includes a portion of the arterial blood supply of the circulatory system.

It is preferable for the system to supply a continuous suprasystolic pressure in both systole and diastole and that the blood pump is positioned in series with the normal blood flow of a circulatory system.

Preferably, the localised hypertensive region is created downstream from the blood pump.

MODES FOR CARRYING OUT THE INVENTION

Some embodiments of the present invention increase the input blood pressure to a limb of a mammal, usually a human patient. By locally increasing the blood pressure, a greater pressure gradient is generated in a distal region of the patient's circulatory system (in this embodiment the distal region is a limb of the patient and thereby greater blood flow is encouraged within the limb).

Increased local blood pressure also increases the partial pressures of the dissolved oxygen leading to better tissue nutrition. The oxygen debt and toxic metabolites that have accumulated are therefore decreased. This increased perfusion is intended to promote healing, encourage development of co-lateral vessels and may reduce other associated symptoms, such as ulceration and pain. The aim is to create a localised area of hypertension at the upper part of the limb arterial system to reverse ischemic changes.

In the lower limbs of a human patient there are three distal arteries. These are the anterior tibial, posterior tibial and peroneal arteries. In peripheral vascular disease, there are different numbers and sizes of collaterals emanating from, or going to, these vessels. Embodiments of the present invention increase the blood pressure and thereby increase blood flow throughout the vessels and in the long term increase collaterisation. This effect also may increase with increased perfusion pressure generated by the embodiment.

Preferably, an optimal collateral flow generally occurs at steady input pressures. The preferred embodiments of the present invention may increase in all three parameters; ie: systolic, mean and diastolic pressures.

An increase in the mean blood pressure within a limb or distal region of the circulatory system may improve neovascularisation. Preferred embodiments of the present invention may create localised areas of hypertension and thereby vascular neogenesis is stimulated, resulting in an improved blood flow circulation throughout the limb.

Figure 1:
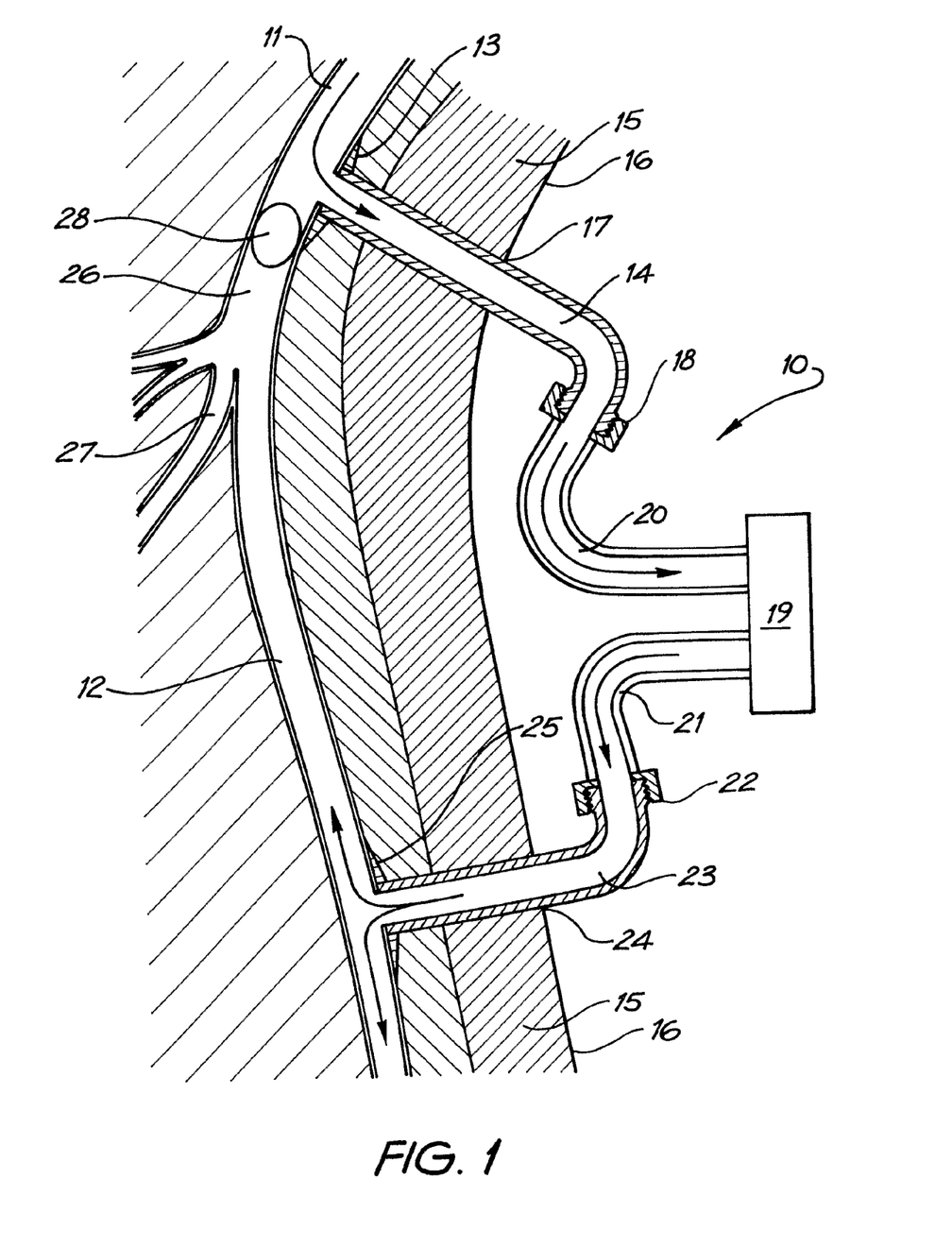
FIG. 1 is a schematic representation of a short term hyper perfusion system according to one embodiment of the invention.

The short-term hyperperfusion system 10 shown schematically in FIG. 1 is connected between a cardiac side artery 11 and, in this instance, the superficial femoral artery 12. The system 10 is connected to the artery 11 by arterial connector 13 at the inner end of an inflow cannula 14 which penetrates through the subcutaneous tissue 15 and the skin line 16 at exit 17.

At the outer end of the cannula 14 there is a threaded connector 18 by means of which the inflow cannula 14 is, connected to the low pressure side of an external medical device 19 such as a blood pump or haemodialysis machine by tubing 20.

The high pressure side of the medical device 19 is connected by tubing 21 to threaded connector 22 at the outer end of an outflow cannula 23 which enters the skin line 16 through entry 24 and penetrates through the subcutaneous tissue 15. The inner end of the outflow cannula 23 is connected to the superficial femoral artery 12 by arterial connector 25.

In this instance, the hyperperfusion system 10 is coupled to the patient's lower limb and the blood is pumped at super-systolic pressures towards the common femoral artery 26 and then to the profunda femoris artery 27. The common femoral artery 26 is occluded by an implanted occlusion device or balloon 28 which selectively blocks flow between the artery 11 and the common femoral artery 26 and essentially allows the pumping system to work in series with the patient's normal circulatory system.

Figure 2:
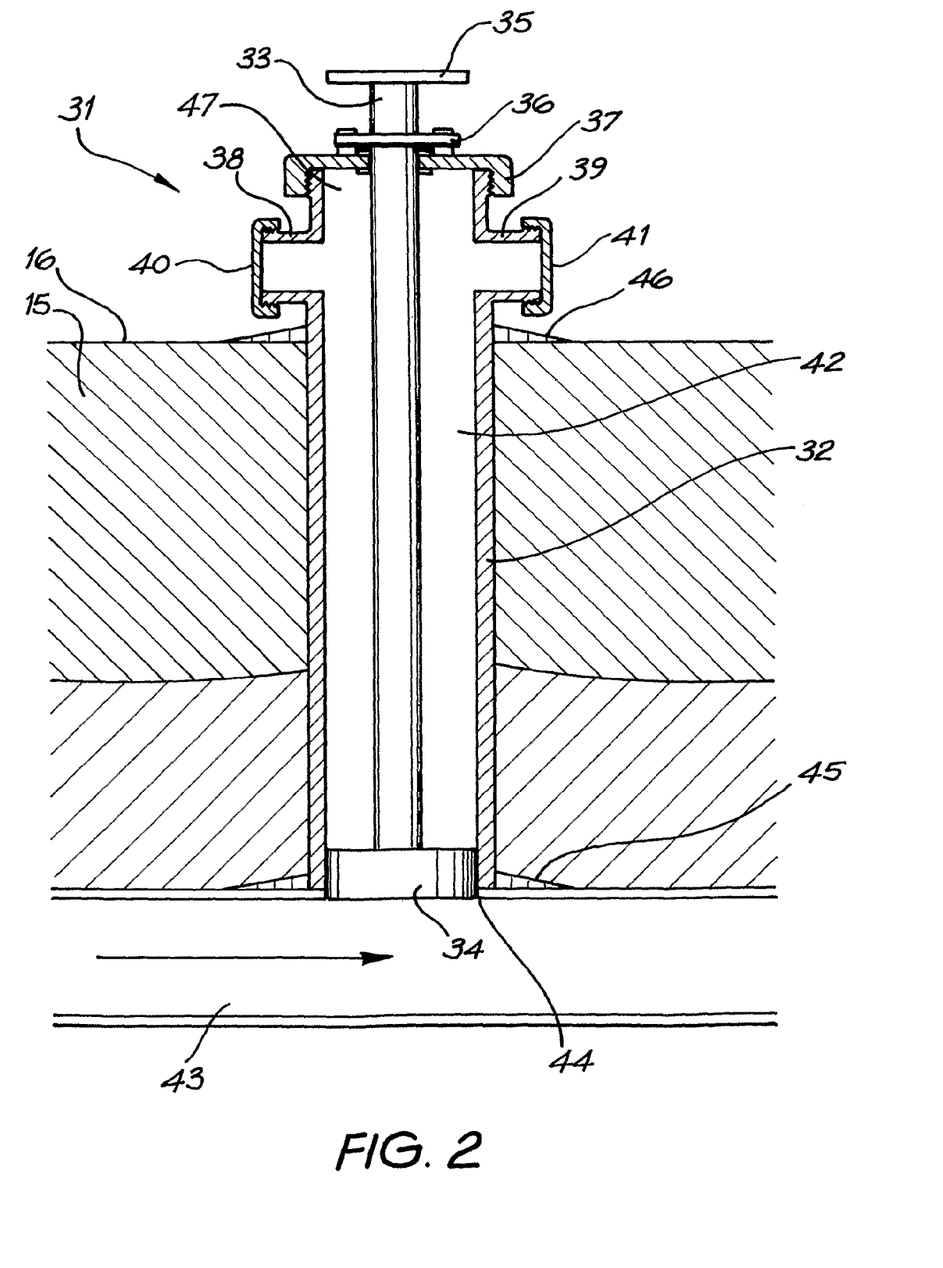
FIG. 2 is a cross sectional view of an inflow cannula of the system shown in FIG. 1 with the plunger extended to prevent blood flow into the cannula.
Figure 3:
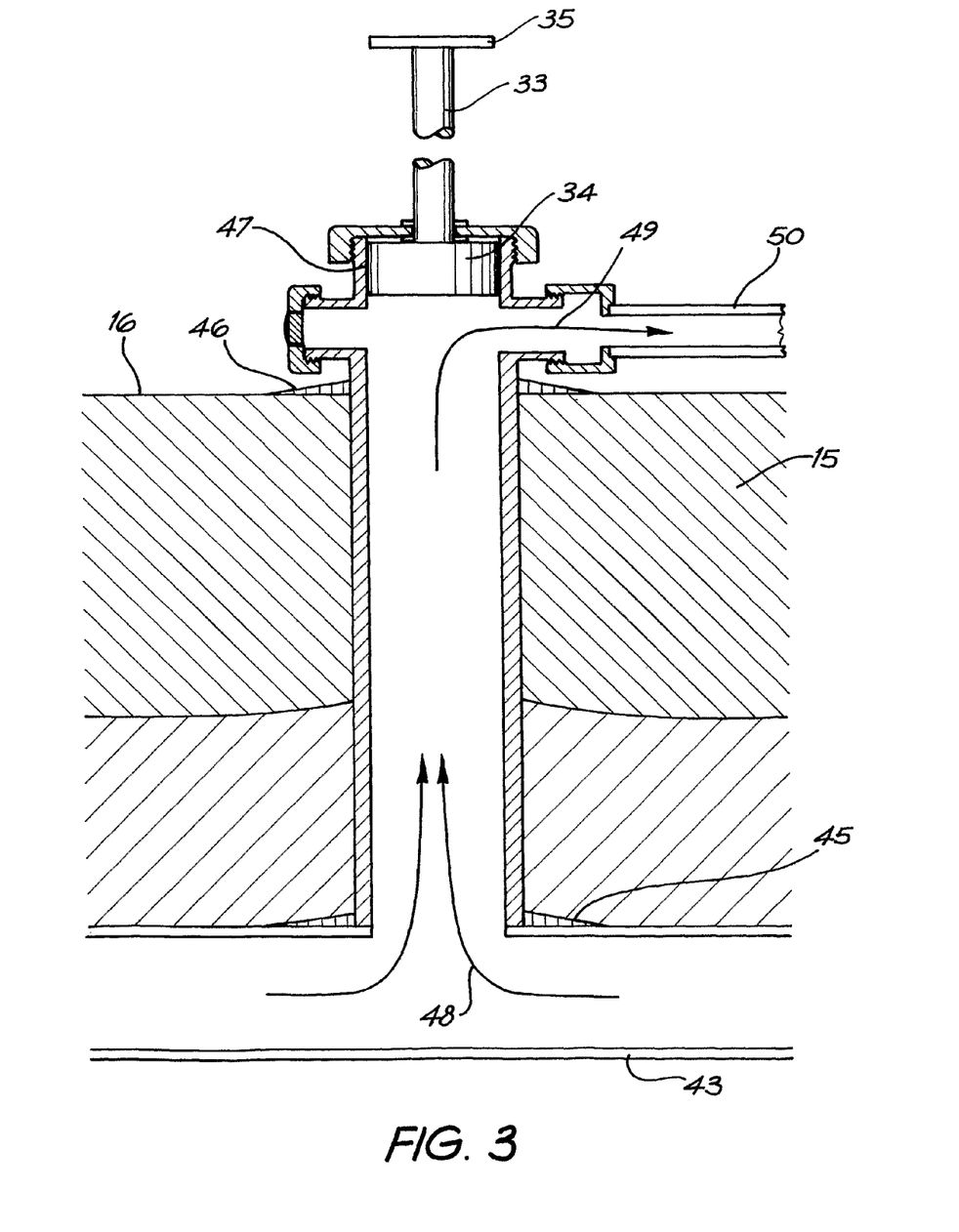
FIG. 3 is a view similar to that of FIG. 2 with the plunger of the cannula retracted to allow blood flow through the cannula.

The cannula shown in FIGS. 2 and 3 is, in effect, a high pressure circulatory access device 31 which has a housing 32, a plunger stem 33 which has a head 34, a handle 35 and a locking pin 36.

The upper end of the housing 32 is closed by detachable cap 37 through which the plunger stem 33 projects. The inflow/outflow port 38 and 39 which are closed by detachable caps 40 and 41 are in fluid communication with the lumen 42 of the access device 31.

As shown in FIGS. 2 and 3, the biocompatible housing 32 extends through the skin line 16 and penetrates the subcutaneous tissue 15 to join artery 43. An arteriotomy 44 allows fluid communication between the artery 43 and the lumen 42.

The plunger head 34 is preferably constructed of a biocompatible material such as Polytetrafluoroethylene in order to minimise thrombogenesis around the arteriotomy 44.

The locking pin 36 is adapted to lock the plunger stem 33 at any desired position to prevent undesired movement of the plunger stem 33 by back pressure of the patient's normal arterial system.

An arterial attachment cap 45 is provided at the arteriotomy 44 to reinforce the connection of the housing 32 to the artery 43. Similarly, at the skin line 16 there is an attachment cap 46 which secures the skin against the housing 32 to minimise movement and to reduce the possibility of infection.

The access device 31 is shown in FIG. 2 with the plunger head 34 in its closed position and in FIG. 3 the plunger head is in its open position where it is positioned in the upper cavity 47 of the housing 32 beyond the port 38 and 39 so as to allow blood flow through the lumen 42 of the cannula 31 as indicated by the arrows 48 and 49. In use, the cap 41 is removed and the port 39 connected to tubing 50 leading to an external blood pump device.

The cap 40 may be selectively removed to allow access to the interior of the device 31 and may allow for the insertion of an occlusion device and/or pharmaceuticals. Lumen 42 may also be filled with sterile antibiotic containing anti-coagulated saline when not in use. The interior of the housing 32 may also be accessed by the removal of cap 40 to remove any residual blood.

Figure 4:
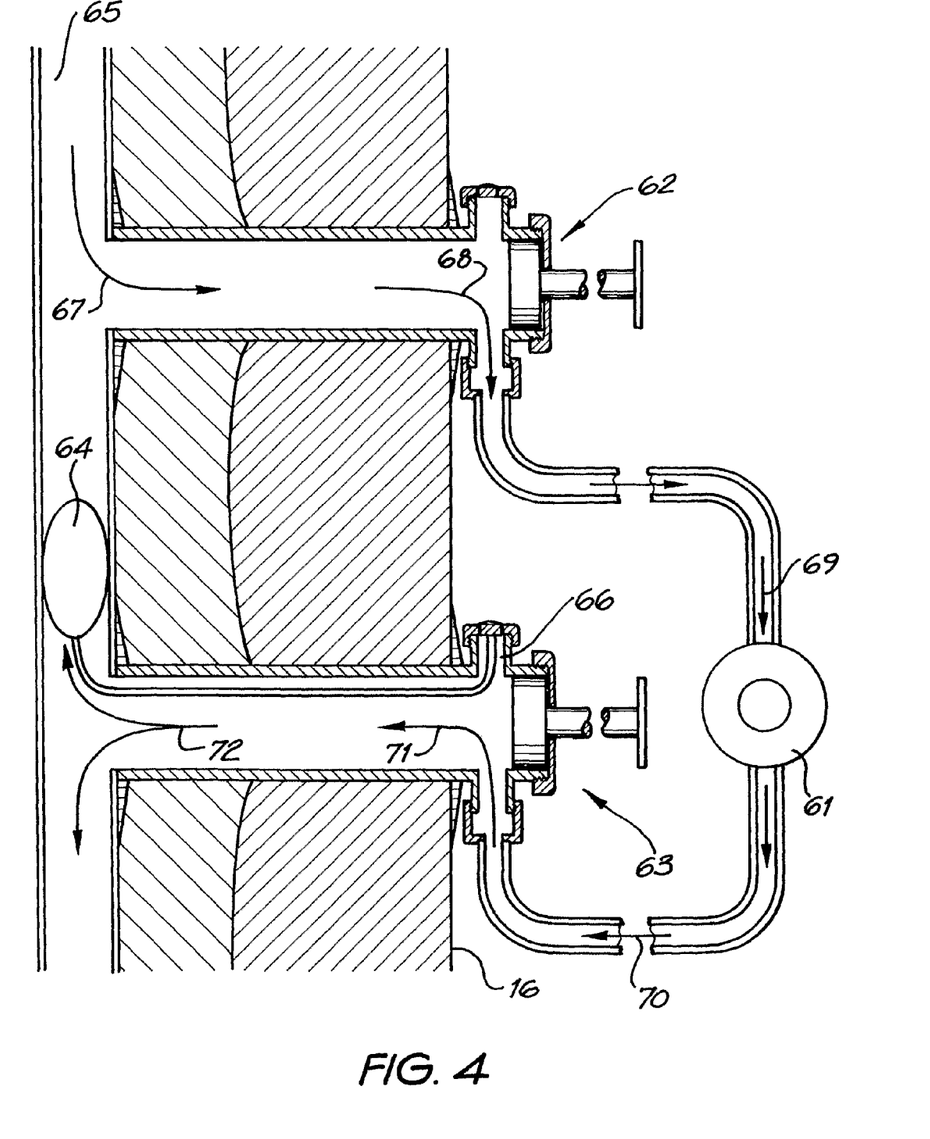
FIG. 4 is a schematic representation of a hyper perfusion system according to a second embodiment of the invention.

The hyperperfusion system 60 shown in FIG. 4 includes a blood pump 61 in fluid communication with an inflow cannula 62 and an outflow cannula 63 both of which incorporate a high pressure circulatory access device as shown in FIGS. 2 and 3. An occlusion device 64 is positioned within the artery 65 after passing through the port 66 in the cannula 63. Blood flow is shown by arrows 67, 68, 69, 70, 71 and 72.

Figure 5:
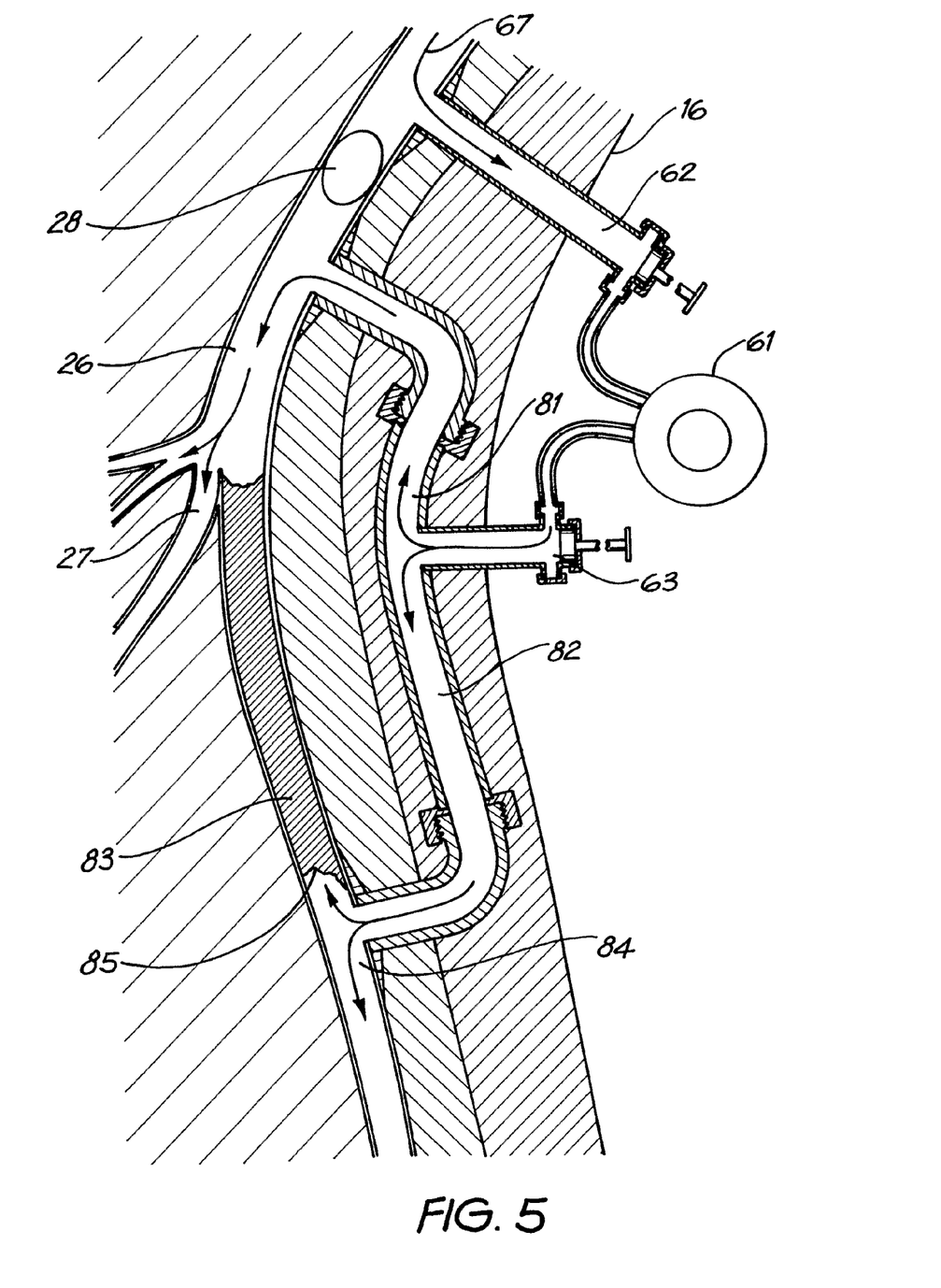
FIG. 5 is a schematic representation of a hyper perfusion system according to a third embodiment of the invention.

The hyperperfusion system 80 shown in FIG. 5 is a modification of that shown in FIG. 4 in that the outflow cannula is divided downstream into a first outflow cannula portion 81 and a second outflow cannula portion 82. The first portion 81 is connected to the common femoral artery 26 and the second portion 82 is connected to the profunda femoris artery 84 which, in the section 83 is occluded by an occlusion device 85.

The circulatory access device need not be of the plunger type as described above as other kinds of access devices which permit intermittent connection between the circulatory and perfusion systems may be used. For example, the access device may be a percutaneously controllable valve which, when open, permits access between the circulatory system and the perfusion system. Such a valve may be constructed from metal, tissue or polymeric material. The valve may incorporate a tilting disc, flap, ball or membrane as its flow control means.

Figure 6:
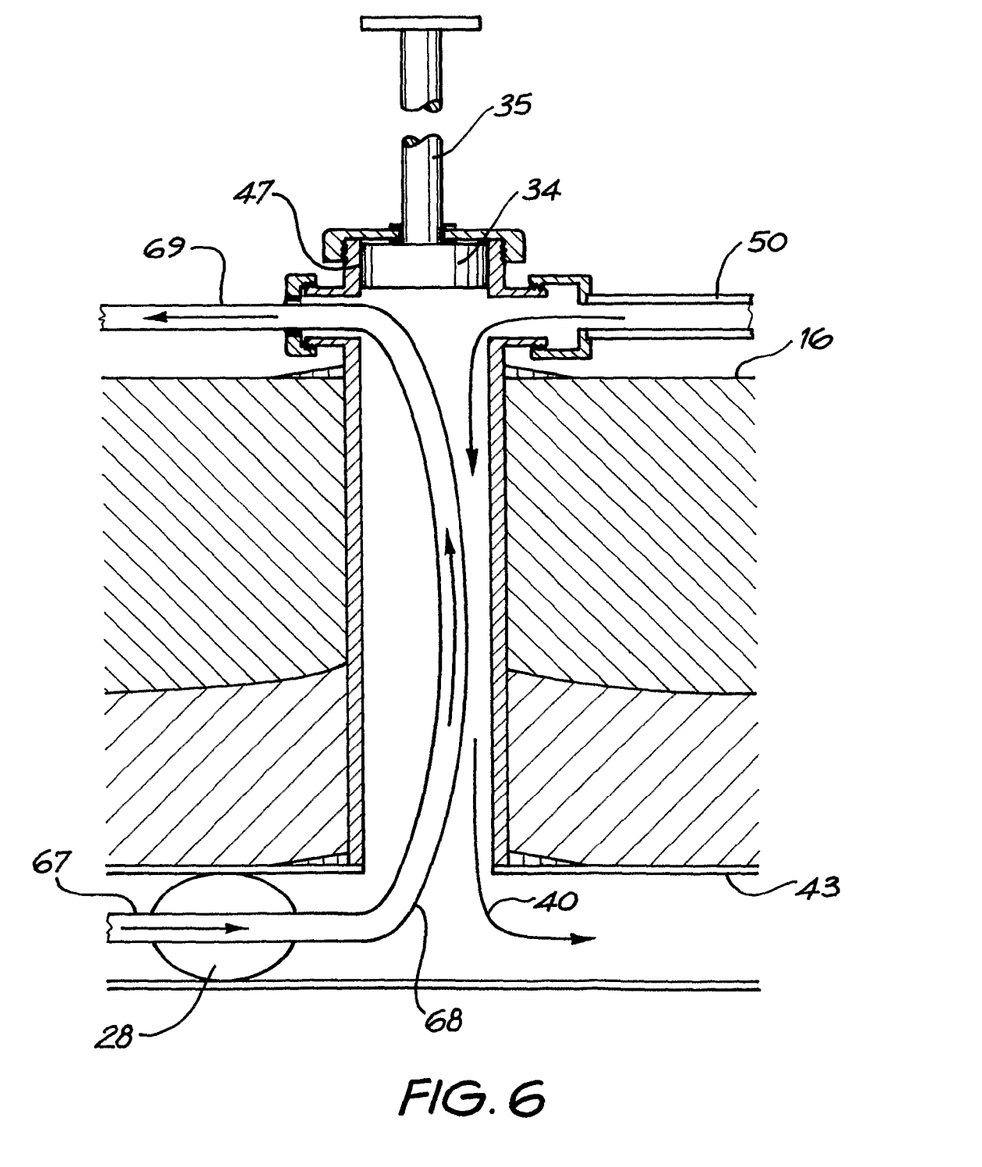
FIG. 6 is a schematic representation of a hyper perfusion system according to a fourth embodiment of the invention.

The continuous access device 47 shown in FIG. 6 is somewhat similar to that shown in FIGS. 2 and 3 except that a single device is used for both blood flows. The components of the embodiment of FIGS. 2 and 3 which are common to the embodiment of FIG. 6 carry the same reference numerals. In this instance, the balloon catheter 28 located in the native vessel 43 surrounds the lower end of blood flow tubing 68 having an inlet 67 and an outlet 69 connected to the blood pump. Inflow of blood into the vessel 43 from the pump is via tubing 50 at suprasystolic pressure. The skin is represented by numeral 16 and the direction of return flow at suprasystolic pressures is indicated by arrow 40.

Figure 7:
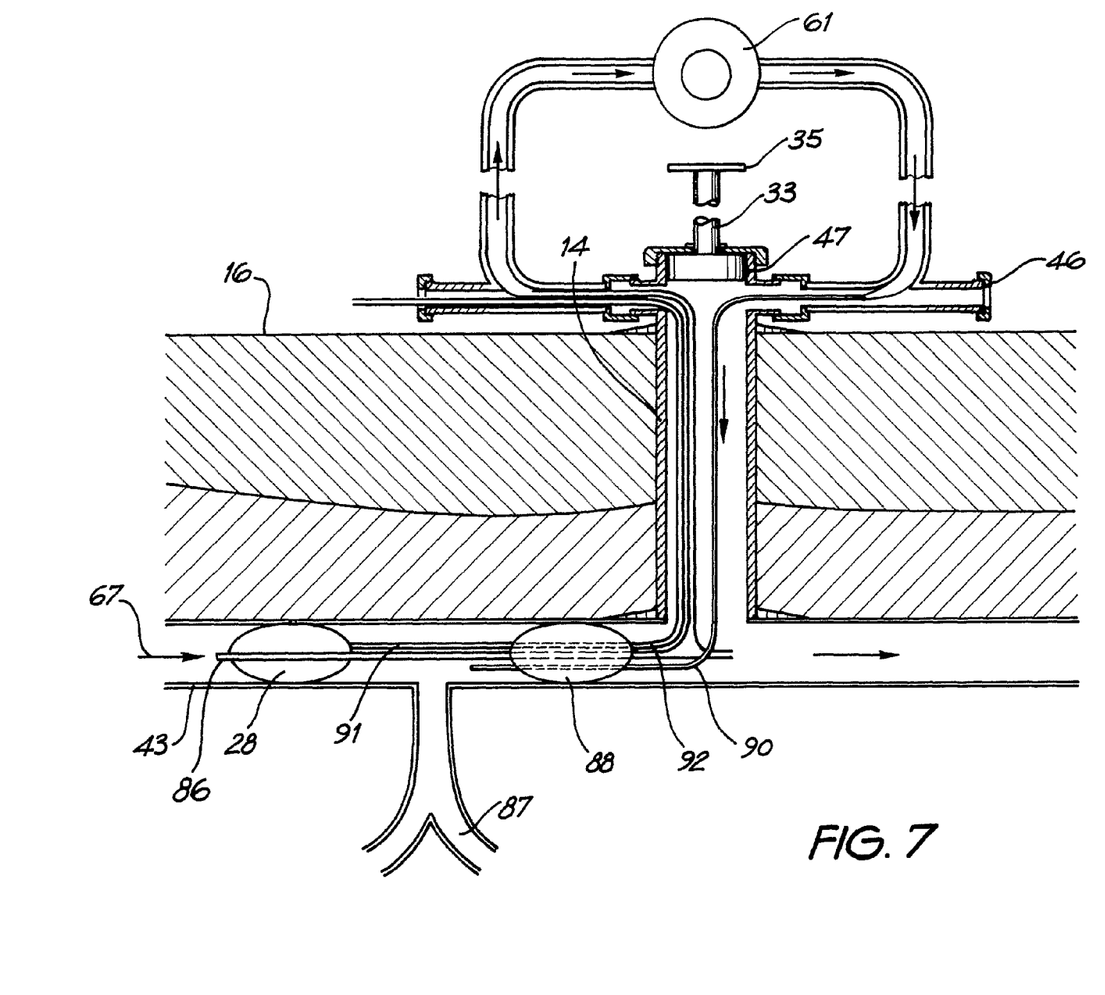
FIG. 7 is a schematic representation of a hyper perfusion system according to a fifth embodiment of the invention.

The right and left internal mammory arteries (RIMA, LIMA) are often used to bypass obstruction to the coronary arteries. Isolation of these or other similar vessels is shown in FIG. 7. The main supply artery 43 which may be subclavian, aorta, iliac or femoral vessels has a proximal balloon 28 connected to the inflating catheter 91. Numeral 67 indicates the entry of the proximal balloon catheter 28. Downstream of the target artery 87 which may be RI MA, LIMA, renal or distal vessels is a distal balloon 88 connected to the deflating catheter 92. The hyperperfusion catheter is indicated by numeral 90 and the main inflow reinforced tubing by numeral 86.

Figure 8:
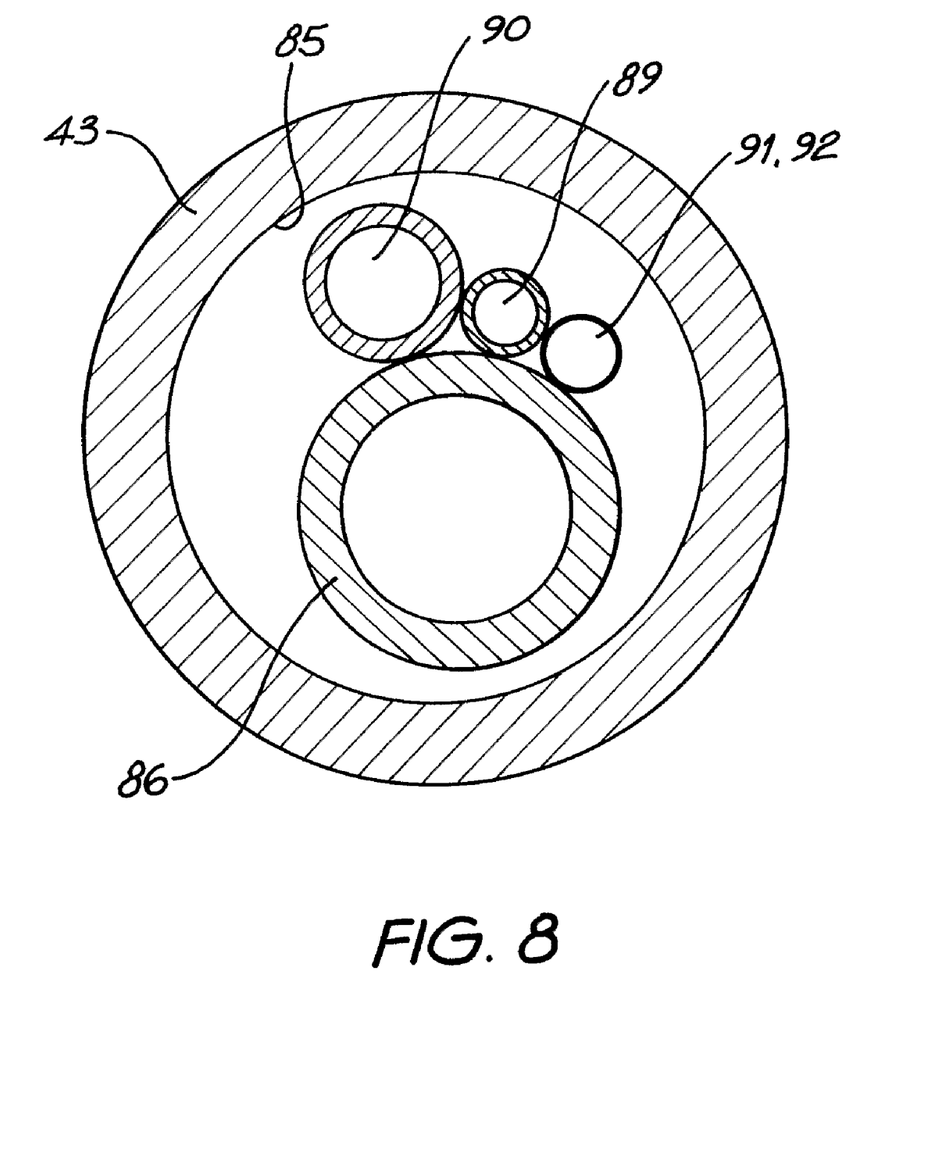
FIG. 8 is a cross sectional view of the tubing system of FIG. 7.

The tubing system of this embodiment of the invention shown in cross section in FIG. 8 consists of an inflow reinforced catheter 86 around which is located a pressure sensing system 89, inflating, deflating catheter 91 for the proximal balloon 28, inflating and deflating balloon catheter 92 for the distal balloon 88 and the hyperperfusing catheter 90 from the blood pump, all of which are located within the inner wall 85 of the main supply artery 43. The entire balloon system may be introduced for long term use by the continuous access device 14 or transcutaneously.

Figure 9:
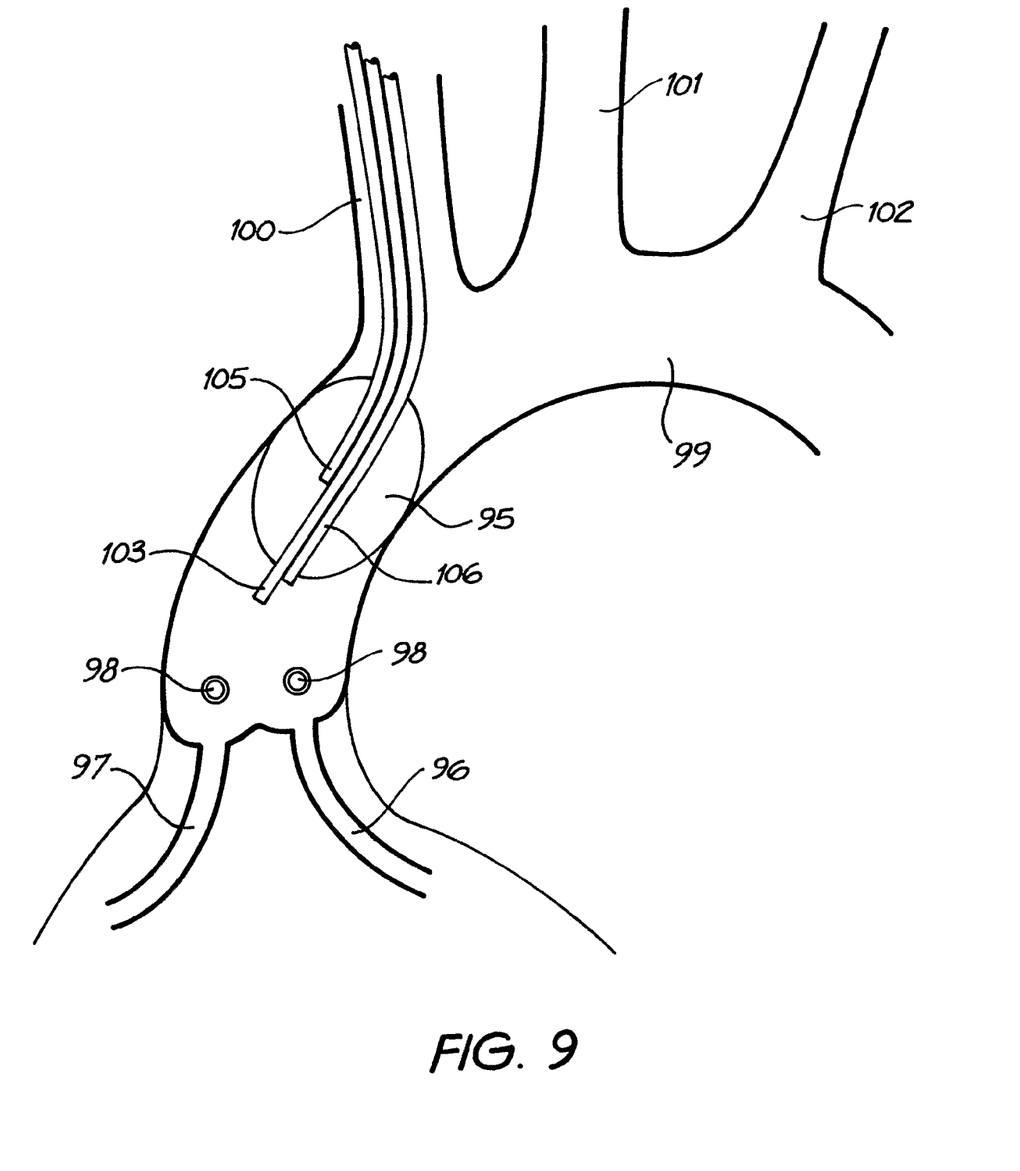
FIG. 9 is a schematic representation of a hyper perfusion system according to a sixth embodiment of the invention.

FIG. 9 shows a further embodiment of the invention in which the access system is combined with intermittent inflation of a balloon in the aorta in diastole. In this situation, hyperperfusion of the coronary artery bypass grafts or the coronary arteries themselves is achieved in diastole. In this embodiment of the invention, the aim is to increase the pressure between the inflation balloon 95 and the origins of the left coronary artery 96 and the right coronary artery 97 and the coronary artery bypass graft origins 98. As can been seen in FIG. 9, the descending aorta is identified by numeral 99.

The brachiocephalic trunk is 100, the left common carotid artery is 101 and the left subclavian artery is 102. The balloon is occlusive or semi-occlusive in diastole in the ascending aorta and the pressure through the infusion catheter 103 is increased to supradiastolic or even suprasystolic pressures. The balloon is inflated not to displace volume as the standard pulsation system, but to create an isolated segment in order to hyperperfuse the vessels between the balloon and the closed aortic valve. The result is a very large increase in coronary artery flow or coronary artery bypass flow. The balloon infusion catheter is 105 which has to be large enough to occlude or partially occlude, to inflate and deflate during diastole. The pressure sensing catheter 106 is used to measure the pressure within the hyperperfused isolated segment.

Figure 10:
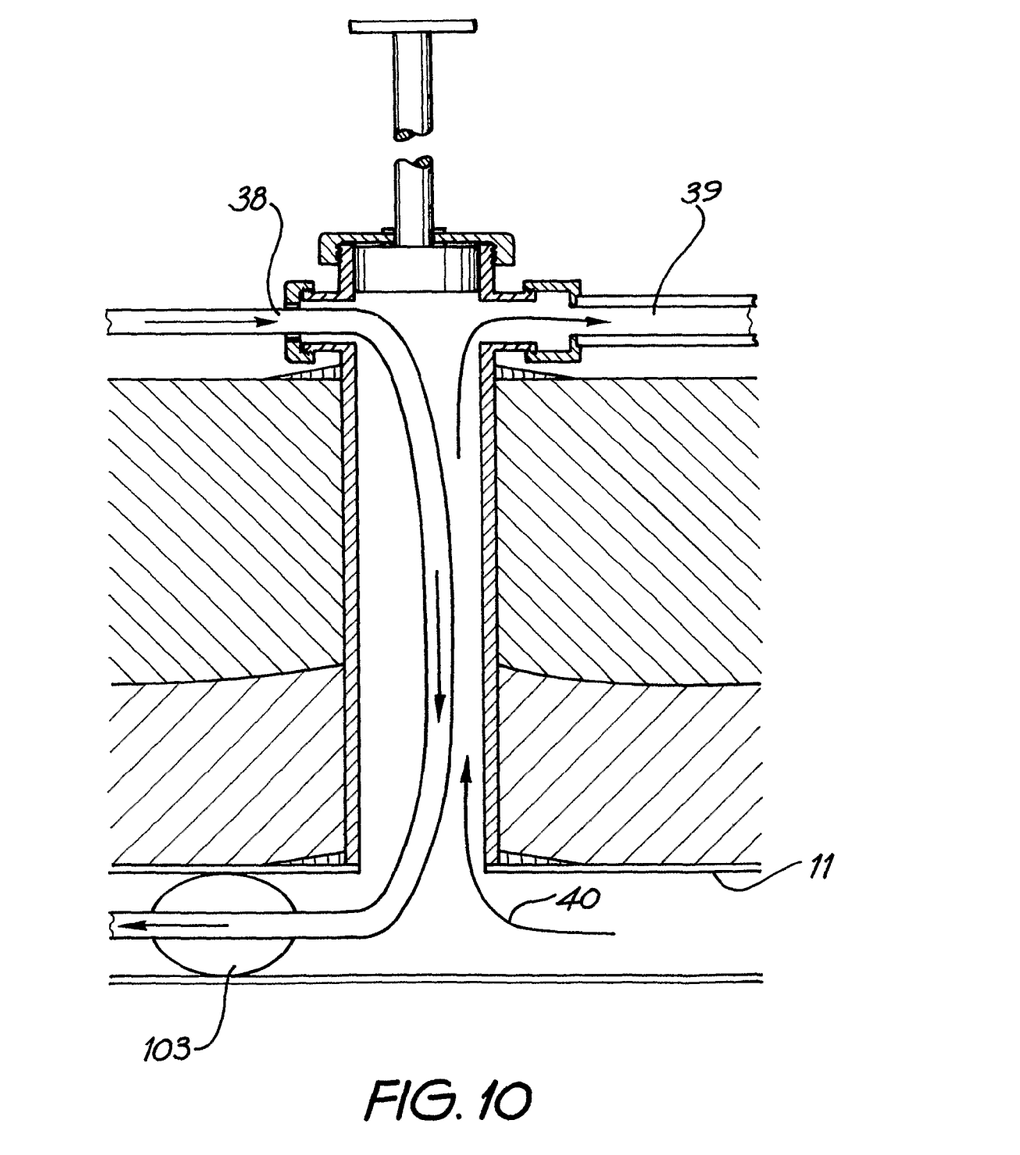
FIG. 10 is a schematic representation of a hyper perfusion system according to a seventh embodiment of the invention.

In FIG. 10 the blood flow through the access device is different from some other applications. The inflow to the pump 39 is in direct connection with the donor vessel 11. The direction of flow indicated by arrow 40 towards the pump 38 is augmented and returned to the target vessel. For example, the right subclavian artery receives inflow during systole which is then augmented with the pump 38 and returned to the closed segment in the ascending aorta. The hyperperfusing cardiac catheter is 103, the other end is in the ascending aorta.

Figure 11:
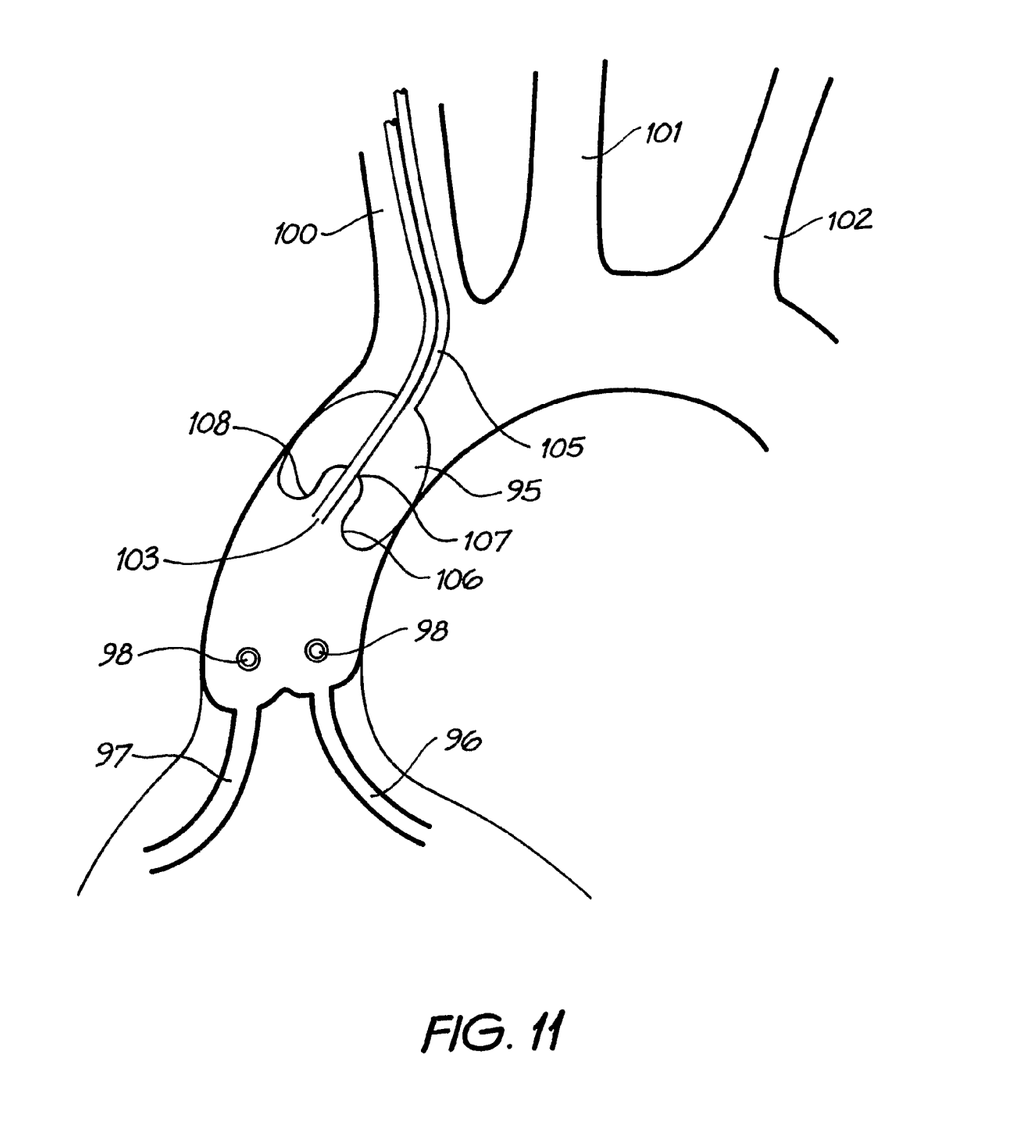
FIG. 11 is a schematic representation of a hyperperfusion system according to the seventh embodiment of the invention.

A further embodiment of the invention is shown in FIG. 11 where the balloon system itself acts as a generator of hyperperfusion, i.e. above normal coronary flow pressures and therefore increases coronary flow. In this situation, no separate hyperperfusion pump is required. The balloon 95 within the aorta expands indiastole only, creating a closed segment between the balloon 95 and the left and right coronary artery orifices 98. The volume within the balloon segments 106, 107 and 108 contracts increasing the volume and pressure within the closed segment between the balloon 95 and the coronary artery orifices 98. The pressure and flow in the coronary arteries therefore increases, the total increase in flow will depend upon the volume of the segments 106, 107 and 108. The pressure generated is greater than a standard counterpulsation balloon system.

As will be apparent from the foregoing description, the access systems of the invention may be used to hyperperfuse any vessel (natural, man made or of animal origin) in the body. A single lumen may be used for the inlet and outlet by containing the inflow and outflow cannula within the same lumen.

It will also be appreciated that the access systems can be inserted percutaneously when required and removed entirely when not needed. The access systems may also be adapted for isolated short term acute hyperperfusion such as the situation in a trauma room when acute access is required to save a limb.

The various forms of the access device may contain one or more valves positioned along the length of the cannula to control blood flow.

The access devices should be manufactured by materials which are capable of withstanding supra-systolic pressures, enable the device to be sutured in place to allow for tissue ingrowth and may be made from composite or non composite materials being man made, human or of animal origin.

The access devices of the invention may be used in an end-to-end or an end-to-side arrangement. The attachment of the device can be made either end-to-end wherein the end of the access device is straight or attachment can be made at an angle of between 0° and 180° relative to the vessel wall.

The plunger may be adapted to provide for drug delivery and contrast agents for angiograms being delivered without removing the plunger.

The devices of the invention may be reusable. For example, the device can be cut just below the skin line and a stopper put in place to remove the dead space between the end of the device and the vessel thereby preventing thrombus formation. In the case where reintervention is required, the stopper can be removed percutaneously or by direct incision and a second, extension, piece added and vessel access achieved.

Various modifications may be made in details of design and construction without departing from the scope and ambit of the invention.

The claims defining the invention are as follows:

1. A system of cannulation for perfusing a patient's arterial system so as to stimulate the growth of blood vessels, said system of cannulation being adapted for connection to a blood pump, the system of cannulation comprising:

(i) an inflow cannula having a first end adapted to be connected to said arterial system and a second end adapted to be connected to the blood pump, the inflow cannula including a first slidable plunger operable to open and close the inflow cannula and being intermediate the first and second ends of the inflow cannula, (ii) an outflow cannula having a first end adapted to be connected to the blood pump and a second end adapted to be connected to said arterial system at a location downstream from the first end of the inflow cannula, the outflow cannula including a second slidable plunger operable to open and close the outflow cannula and being intermediate the first and second ends of the outflow cannula, the arrangement being such that blood flow from the pump is in series with the normal blood flow of the arterial system of the patient and is increased by operation of the pump when the inflow and outflow cannulas are open so as to create a localized region of hypertension for stimulating the growth of blood vessels in the arterial system requiring perfusion, wherein an occlusion device is inserted between a high and a low pressure side of the system, and wherein the system supplies a continuous supra-systolic pressure of blood flow in both systole and diastole.

2. A cannulation system according to claim 1 wherein the slidable plunger is lockable when operated to open or close the cannula.

3. A cannulation system according to claim 1 wherein the occlusion device is controlled transcutaneously.

4. A cannulation system according to claim 1 wherein the outflow cannula is divided to provide two outlets.

5. A cannulation system according to claim 1 including an additional outlet for connection to a haemodialysis system.

6. A cannulation system according to claim 1 further including a port to allow simultaneous infusion of pharmaceuticals.

7. A cannulation system according to claim 1 further including a percutaneously controllable valve.

8. A cannulation system according to claim 7 wherein the valve is constructed from metal, tissue or polymeric material.

9. A cannulation system according to claim 7 wherein the valve incorporates a tilting disc, flap, ball or membrane as its flow control means.

10. A cannulation system according to claim 1 wherein the occlusion device is an occlusive or semi-occlusive balloon adapted to increase diastolic pressure in the ascending aorta beyond that generated by the heart in both diastole and systole.

11. A blood pumping system for perfusing a distal region of a patient's circulatory system, said blood pumping system comprising:
(i) a blood pump,
(ii) an inflow cannula having a first end adapted to be connected to said circulatory system and a second end connected to the blood pump, the inflow cannula including a first slidable plunger operable to open and close the inflow cannula and being intermediate the first and second ends of the inflow cannula,
(iii) an outflow cannula having a first end connected to the blood pump and a second end adapted to be connected to said circulatory system at a location downstream from the first end of the inflow cannula, the outflow cannula including a second slidable plunger operable to open and close the outflow cannula and being intermediate the first and second ends of the outflow cannula, the arrangement being such that blood flow from the pump is in series with the normal blood flow of the circulatory system of the patient and creates a localized hypertensive region in the distal region for stimulating the growth of blood vessels in the arterial system requiring perfusion, wherein an occlusion device is inserted between a high and a low pressure side of the system, and wherein the system supplies a continuous supra-systolic pressure in both systole and diastole.

12. A blood pumping system according to claim 11 wherein the distal region includes a portion of the arterial blood supply of the circulatory system.

* * * * *